(12) United States Patent
Eberle

(10) Patent No.: US 8,583,218 B2
(45) Date of Patent: Nov. 12, 2013

(54) OPTICAL IMAGING PROBE CONNECTOR

(75) Inventor: Michael J. Eberle, Fair Oaks, CA (US)

(73) Assignee: Vascular Imaging Corporation, Rancho Cordova, CA (US)

( * ) Notice: Subject to any disclaimer, the term of this patent is extended or adjusted under 35 U.S.C. 154(b) by 524 days.

(21) Appl. No.: 12/609,123

(22) Filed: Oct. 30, 2009

(65) Prior Publication Data

US 2010/0113942 A1     May 6, 2010

Related U.S. Application Data

(60) Provisional application No. 61/110,345, filed on Oct. 31, 2008.

(51) Int. Cl.
    *A61B 1/00*     (2006.01)

(52) U.S. Cl.
    USPC .................. 600/478; 356/241.1; 359/341.1; 385/39

(58) Field of Classification Search
    USPC ......... 600/309, 325, 327, 332, 339, 342–343, 600/473, 476, 478
See application file for complete search history.

(56) References Cited

U.S. PATENT DOCUMENTS

| | | | |
|---|---|---|---|
| 3,922,064 | A | 11/1975 | Clark et al. |
| 4,116,655 | A | 9/1978 | Lewis |
| 7,184,148 | B2 | 2/2007 | Alphonse |
| 7,190,464 | B2 | 3/2007 | Alphonse |
| 7,242,480 | B2 | 7/2007 | Alphonse |
| 7,242,832 | B2 | 7/2007 | Carlin et al. |
| 7,417,740 | B2 | 8/2008 | Alphonse et al. |
| 2004/0067000 | A1 | 4/2004 | Bates et al. |
| 2007/0116408 | A1 | 5/2007 | Eberle et al. |
| 2008/0077225 | A1 | 3/2008 | Carlin et al. |

FOREIGN PATENT DOCUMENTS

| | | |
|---|---|---|
| EP | 1001290 A1 | 5/2000 |
| JP | 2012507753 A | 3/2012 |
| WO | WO-2008/100774 A1 | 8/2008 |
| WO | WO-2010051401 A1 | 5/2010 |

OTHER PUBLICATIONS

"International Application Serial No. PCT/US2009/062675, International Search Report mailed Jan. 20, 2010", 4 pgs.
"International Application Serial No. PCT/US2009/062675, Written Opinion mailed Jan. 20, 2010", 8 pgs.
"International Application No. PCT/US2009/062675, International Preliminary Report on Patentability, mailed May 12, 2011", 9 pgs.
"European Application Serial No. 09745242.9—Exam Notification 94(3) Received", 5 pgs.
"European Application Serial No. 09745242.9, Response filed Mar. 5, 2013 to Examination Notification Art. 94(3) mailed Nov. 7, 2012", 11 pgs.

*Primary Examiner* — Parikha Mehta
(74) *Attorney, Agent, or Firm* — Schwegman, Lundberg & Woessner, P.A.

(57) ABSTRACT

An elongated optical guidewire assembly, such as for optically imaging a patient from within another catheter, can have a lead portion and a probe portion. A connector between the lead and probe portions can include a bore including first and second bore ends. The first bore end can include a substantially circular cross-sectional profile. The second bore end can include a substantially non-circular cross-sectional profile. The bore can be configured to receive the optical guidewire assembly at the first bore end and configured to deform the optical guidewire assembly at the second bore end such that probe and lead ends of the optical guidewire assembly are deformed into a substantially non-circular profile and located between the first and second bore ends.

17 Claims, 14 Drawing Sheets

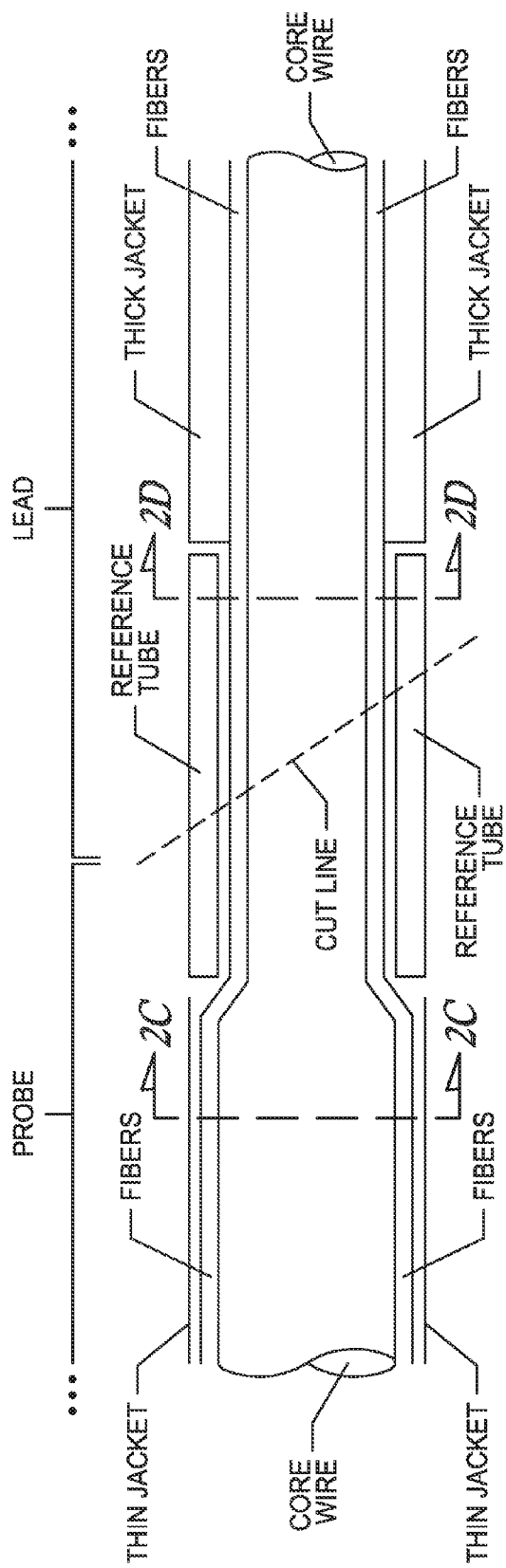
FIG. 2B
FIG. 2C
FIG. 2D

OPTICAL IMAGING PROBE CONNECTOR

CLAIM OF PRIORITY

This patent application claims the benefit of priority of Michael J. Eberle U.S. Provisional Patent Application No. 61/110,345, filed Oct. 31, 2008, which is incorporated herein by reference.

BACKGROUND

Bates et al. United States Published Patent Application US 2004/0067000 discusses a minimally-invasive optical-acoustic device for vascular and non-vascular imaging. It discloses an elongated optical imaging guidewire, catheter, or like probe with one or more ultrasound transducers at its distal end to provide ultrasound energy such as to nearby tissue or the like. Light energy produced at the external instrumentation is transmitted toward the implanted distal end of the instrument, where it is converted to sound energy that can be directed at nearby tissue or the like. Sound energy returned by such tissue modulates light energy at or near the distal end of the implanted section of the instrument. Such modulated light is then communicated to back toward the proximal end of the instrument, and then to externally located diagnostic instrumentation.

Eberle et al. United States Published Patent Application US 2007/01164408, which is incorporated herein by reference, discusses a connector for an optical imaging probe, techniques for aligning the optical fibers at the connector, and techniques for improving light coupling between portions of the probe.

OVERVIEW

This document describes, among other things, methods and apparatuses that can help provide an intermediate connection in a guidewire, such as between (1) a lead portion for connecting to external instrumentation and (2) a probe portion for use within the patient. This can help provide cost-effective, easy, accurate, and fast connection of the guidewire, including helping orient and optically couple one or more optical fibers. The connector can help maintain a profile, such as in the probe portion of the guidewire, which can be made small enough to fit within a guidewire-receiving lumen of a therapeutic catheter.

In an example, an elongated optical guidewire assembly, such as for optically imaging a patient from within another catheter, can have a lead portion and a probe portion. A connector between the lead and probe portions can include a bore including first and second bore ends. The first bore end can include a substantially circular cross-sectional profile. The second bore end can include a substantially non-circular cross-sectional profile. The bore can be configured to receive the optical guidewire assembly at the first bore end and configured to deform the optical guidewire assembly at the second bore end such that probe and lead ends of the optical guidewire assembly are deformed into a substantially non-circular profile and located between the first and second bore ends.

Example 1 can include subject matter including or using an elongated optical guidewire assembly, comprising a longitudinal core wire and a plurality of longitudinal optical fibers arranged about the core wire, the optical guidewire assembly separated into first and second portions that are configured to be optically coupled together at respective first and second ends comprising respective first and second cross-sectional profiles. The subject matter of Example 1 can also include a connector including a bore including first and second bore ends, the first bore end comprising a substantially circular cross-sectional profile and the second bore end comprising a substantially non-circular cross-sectional profile, wherein the bore is configured to receive the optical guidewire assembly at the first bore end and configured to deform the optical guidewire assembly at the second bore end such that the first and second ends of the optical guidewire assembly are deformed into a substantially non-circular profile and located between the first and second bore ends.

In Example 2, the subject matter of Example 1 can optionally include or use the optical guidewire assembly including a deformable tube having an outer diameter, the tube enclosing a portion of the core wire and a portion of the plurality of optical fibers.

In Example 3, the subject matter of any one of Examples 1-2 can optionally include or use the tube being configured to be deformed in the bore, with the tube being separated into a first tube portion and a second tube portion, wherein the first tube portion encloses the first portion of the guidewire assembly at or near the first end of the first portion of the guidewire assembly, and wherein the second portion encloses the second portion of the guidewire assembly at or near the second end of the second portion of the guidewire assembly.

In Example 4, the subject matter of any one of Examples 1-3 can optionally include or use the connector including a ferrule providing at least a portion of the bore.

In Example 5, the subject matter of any one of Examples 1-4 can optionally include or use the second portion of the tube and the second end of the guidewire assembly being attached to the ferrule within the bore near the second bore end.

In Example 6, the subject matter of any one of Examples 1-5 can optionally include or use the connector comprising a handle including the ferrule.

In Example 7, the subject matter of any one of Examples 1-6 can optionally include or use the connector comprising a compression link connected to the handle at a first end and configured to apply a bias force to the ferrule.

In Example 8, the subject matter of any one of Examples 1-7 can optionally include or use the second portion of the tube and the second end of the second portion of the guidewire assembly being attached to the ferrule within the bore at or near the second bore end.

In Example 9, the subject matter of any one of Examples 1-8 can optionally include or use a cleaning element configured to pass through a slot in the ferrule for cleaning the first and second ends of the first and second portions of the guidewire assembly.

In Example 10, the subject matter of any one of Examples 1-9 can optionally include or use an outer diameter of the tube that is between about 343 micrometers (µm) and about 353 µm.

Example 11 can provide, or can optionally be combined with the subject matter of any one of Examples 1-10 to include: providing a length of optical guidewire having a core wire extending substantially the length of the guidewire and a plurality of optical fibers positioned about the core wire and extending substantially the length of the guidewire; enclosing a portion of the guidewire within a deformable tube; providing a ferrule with a bore with a circular cross section at a first end and a non-circular cross section away from the first end; deforming a portion of the tube and the enclosed guidewire using the ferrule; cutting the tube and the enclosed guidewire through the deformed portion of the tube to form a probe portion with a first end and a lead portion with a first end; and providing the ferrule for coupling the first end of the probe portion to the first end of the lead portion.

In Example 12, the subject matter of any one of Examples 1-11 can optionally include deforming a portion of the tube and enclosed guidewire including pushing a portion of the tube and enclosed guidewire through the bore of the ferrule from the first end of the bore through the second end of the bore.

In Example 13, the subject matter of any one of Examples 1-12 can optionally include deforming a portion of the tube and enclosed guidewire includes deforming a portion of the tube and enclosed guidewire from a substantially circular cross section to a substantially square cross section.

In Example 14, the subject matter of any one of Examples 1-13 can optionally include deforming less then 10 mm of the tube and enclosed guidewire to a substantially square cross section.

In Example 15, the subject matter of any one of Examples 1-14 can optionally include cutting the tube and enclosed guidewire, including cutting a slot in the ferrule.

In Example 16, the subject matter of any one of Examples 1-15 can optionally include cutting the tube and enclosed guidewire includes securing the tube and guidewire to the ferrule near the second end of the bore.

In Example 17, the subject matter of any one of Examples 1-16 can optionally include cutting the tube and enclosed guidewire to stabilize relative positions of the core wire and the plurality of optical fibers.

In Example 18, the subject matter of any one of Examples 1-17 can optionally include cutting the tube and enclosed guidewire to stabilize relative positions of the core wire and the plurality of optical fibers using a flowable and later hard-enable substance.

In Example 19, the subject matter of any one of Examples 1-18 can optionally include cutting the tube and enclosed guidewire, including cutting the tube and enclosed guidewire at an oblique angle to the length of the guidewire.

In Example 20, the subject matter of any one of Examples 1-19 can optionally include coupling the first end of the probe portion to the first end of the lead portion, wherein coupling the first end of the probe portion to the first end of the lead portion includes inserting the first end of the probe portion into the first end of the ferrule.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1 shows an example of a lead portion and probe portion of an example of an optical guidewire assembly, and a sleeve connector there between.

FIGS. 2A, 2B, 2C, and 2D show examples of a lead portion, a probe portion and a sleeve connector of an example of an optical guidewire assembly that includes an example of an alignment groove.

DETAILED DESCRIPTION

The present inventors have recognized, among other things, that an imaging guidewire, or optical guidewire, can be made small enough to fit within a lumen of a therapeutic catheter. To help while placing or exchanging such a therapeutic catheter, the guidewire can be disconnected at an intermediate location along the length of the guide wire. The disconnected guidewire can be made to fit completely within the catheter lumen. The guidewire can be easy for a physician to disconnect or re-connect such as at a location within the sterile field, which can be wet and bloody. In an example, a single mode optical fiber core can be less than 10 μm in diameter. A small misalignment between optical fiber cores can produce significant optical coupling loss. Efficient coupling of light between respective ends of multiple pairs of approximately parallel optical fibers along a guidewire can be difficult, such as when using fiber cut from different guidewire regions, or when optically coupling different guidewires. Relative spatial variations of the optical fibers running along a length of a guidewire can make it difficult to mechanically align the fiber ends of different regions of the guidewire or to align the ends of different guidewires.

This document describes, among other things, methods and apparatuses that can help provide an intermediate connection in a guidewire, such as between (1) a lead portion for connecting to external instrumentation and (2) a probe portion for use within the patient. This can help provide cost-effective, easy, accurate, and fast connection of the guidewire, including helping orient and optically couple one or more optical fibers. The connector can help maintain a profile, such as in the probe portion of the guidewire, which can be made small enough to fit within a guidewire-receiving lumen of a therapeutic catheter.

Figure 1:
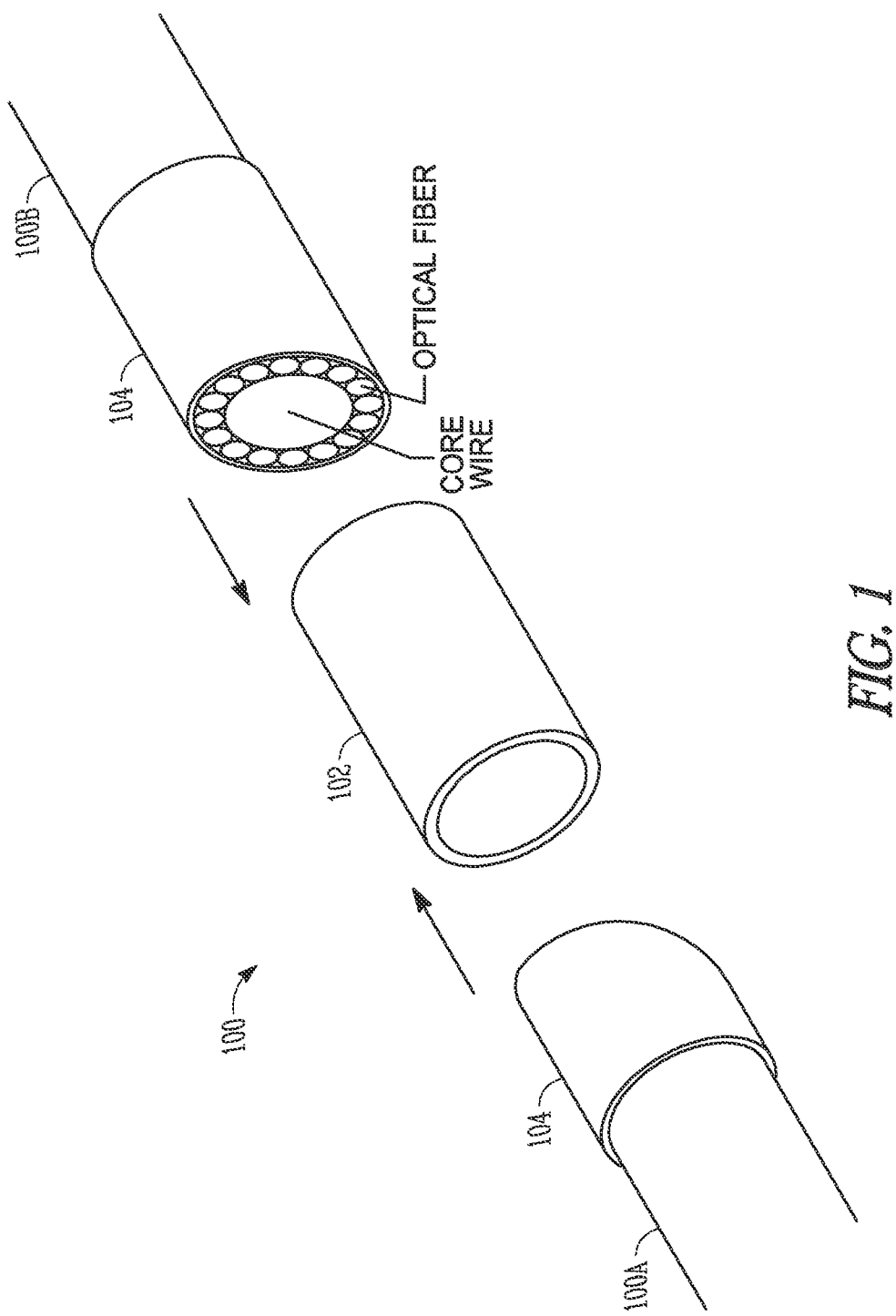

FIG. 1 shows an example of a lead portion 100A and probe portion 100B of an example of an optical guidewire assembly 100 ("guidewire"), and a sleeve connector 102 therebetween. In an example, a single length of the optical guidewire 100 can be cut to form the lead portion 100A and the probe portion 100B of the guidewire 100. Before such cutting, a precision diameter thin-walled tube 104 can be threaded onto the guidewire 100 to the particular location to be cut. The tube 104 and the guidewire 100 can then be cut, such as to form the lead portion 100A and the probe portion 100B of the guidewire assembly 100. Each such cut end of the guidewire assembly 100 can include a length of the precision thin-walled tube 104.

In an example, the connector 102 can include a reference cylinder with a precision bore such as for receiving the inserted cut ends of the guidewire assembly 100. In an example, the probe portion 100B and the lead portion 100A of the guidewire assembly 100 result from a length of guidewire that has been cut at an oblique angle. The guidewire can include a central core wire, around which optical fibers can be circumferentially affixed. The angled cut can help provide an alignment reference, such as for self-aligning during reconnecting the probe portion 100B and lead portion 100A of the guidewire assembly 100. When properly aligned in the connector, each optical fiber end in the probe portion 100B of the guidewire 100 will align with the corresponding optical fiber end in the lead portion 100A of the guidewire 100 that was cut apart therefrom. In the example of FIG. 1, it can be difficult to obtain a thin-walled tube 104 with a consistent manufacturing tolerance to permit accurate alignment of the ends of the optical fibers of the guidewire assembly 100 within the reference cylinder provided by the thin-walled tube 104.

In some examples, the connector 102 can include a split sleeve reference cylinder. The split sleeve reference cylinder can include a longitudinal split in the cylinder that can help provide an at least slightly expandable and relaxable bore. When relaxed, the bore can be slightly smaller in cross-section than the cut ends of the guidewire assembly 100. In an example, coupling the cut ends of the guidewire 100 can include sliding such ends into the split sleeve cylinder of the connector 102. As such ends enter the cylinder of the connector 102, the longitudinal split in the cylinder allows its bore to expand. This can help accommodate the slightly larger cross-sectional profiles of the ends. The expansion of the bore can help create a crimp-like bias, such as to help secure the cut ends within the reference cylinder of the connector 102. In an example, the reference cylinder of the connector 102 can include a ceramic reference cylinder, such as an aluminum oxide ceramic reference cylinder. In an example, the reference cylinder of the connector 102 can include a metal split sleeve reference cylinder. In an example the split sleeve reference cylinder of the connector 102 can have a bore inner diameter of at least one 1 mm, and can create enough friction to deform the thin-walled tube.

FIGS. 2A-2D show examples of a lead portion 100A, a probe portion 100B and a sleeve connector 102 of an example of an optical guidewire assembly 100 that includes an example of an alignment groove or slot 200. In an example, a single length of optical guidewire 100 can be cut to form the lead portion 100A and the probe portion 100B of the guidewire 100. Before such cutting, the guidewire 100 can be inserted through a reference tube 202. In this example, the reference tube 202 can have a thick enough wall to provide an alignment groove therein. When the diameter of the guidewire 100 is to fit within the lumen of a catheter, the reference tube 202 can have a wall thickness that can require the guidewire to have a smaller core diameter along the lead portion 100A (FIG. 2D) than along the probe portion 100B (FIG. 2C) of the finished guidewire assembly 100. The reference tube 202 can be slipped onto the guidewire 100, such as from the lead portion 100A of the guidewire 100, such as to a location at which the core wire of the guidewire 100 increases in diameter. The reference tube 202 can then be secured to the guidewire 100 at such location, and a cut can be made through both the tube 202 and the guidewire 100. In this example, each cut end of the guidewire assembly 100 can include a length of the reference tube 202.

Figure 2A:
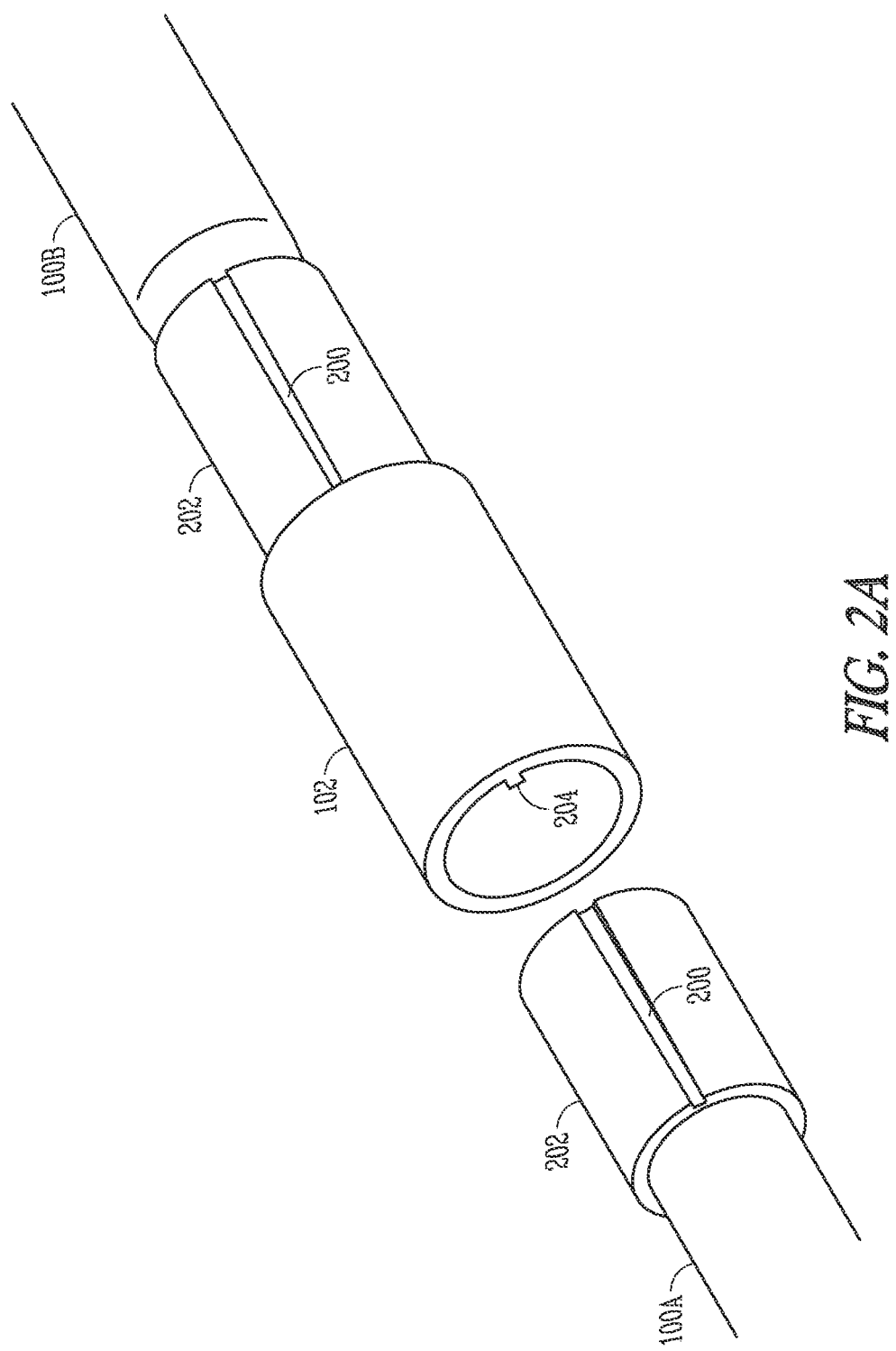

In the example of FIG. 2A, the connector 102 can include a reference cylinder that can include a precision bore such as for receiving inserted reference tubes 202 of each of the cut ends of the guidewire assembly 100. The lead portion 100A of the guidewire assembly 100 can be inserted into one end of the reference cylinder of the connector 102. The probe end 100B of the guidewire assembly 100 can be inserted into the other end of the reference cylinder of the connector 102. The reference cylinder of the connector 102 can include an alignment key 204. The key 204 can inhibit inserting the lead portion 100A or the probe portion 100B of the guidewire assembly 100 into the reference cylinder of the connector 102, unless it engages the alignment slot 200 of the reference tube 202 at each cut end of the guidewire assembly 100. In an example, the reference tube 202 can include tapered alignment slots 200, such as with a wider slot closer to the end to help align or insert the cut ends of the guidewire assembly 100 into the reference cylinder of the connector 102. Alternatively or additionally, the alignment key 204 can similarly be tapered, such as for the same reasons. The example of FIGS. 2A-2C also shows an obliquely angled cut of the guidewire 100, such as for promoting self-alignment, such as discussed above. In the example of FIGS. 2A-2C, manufacturing tolerances can limit the ability to insert the thin-walled reference tubes 202 into the keyed reference cylinder of the connector 102 without deforming the thin-walled metal reference tubes 202 and displacing or otherwise disturbing the optical fibers carried therewithin. The examples of FIGS. 2A-2C can be complex and cumbersome to prototype in a manner that provides consistent fit and function.

Figure 3A:
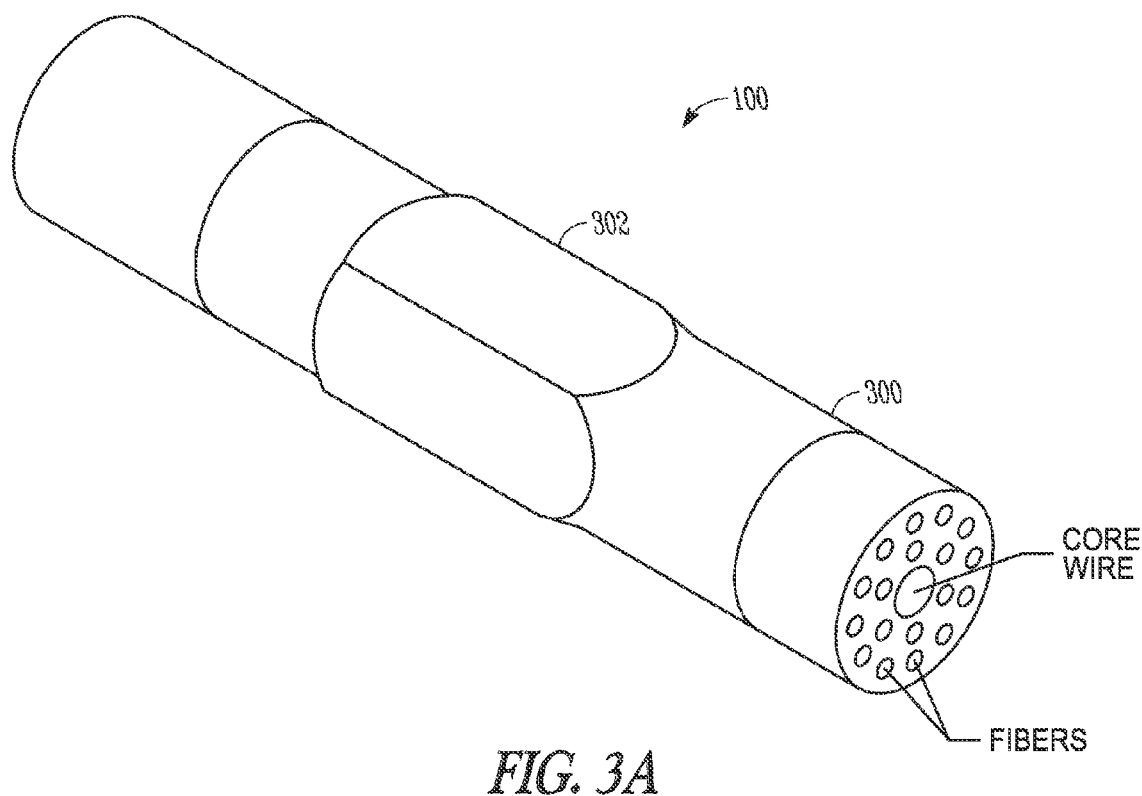
FIG. 3A shows an example of an optical imaging guidewire assembly.

FIG. 3A shows an example of an optical imaging guidewire assembly 100. In this example, the guidewire assembly 100 can include a thin-walled malleable or otherwise deformable tube 300 extending about at least a portion of the guidewire 100. At a particular location, the tube 300 can be deformed, such as into a deformed area 302 having a substantially square shape. After the guidewire assembly 100 is deformed, material can be injected or otherwise introduced into the guidewire 100, such as to stabilize the position of the core wire and the optical fibers in the deformed area 302. In an example, the guidewire 100 can include a curable medium as the injected or otherwise introduced material. After the guidewire 100 and the thin-walled tube 300 are deformed, the medium can be cured to harden it, such as to stabilize the position of the core wire and the optical fibers. The guidewire 100 can then be cut at the deformed area 302, such as at an oblique angle to assist in self-alignment, in an example. The resulting portions of the guidewire assembly 100 can include cut ends having mirror images of each other, such as with respect to the relative positions of the core wire and the optical fibers. The square cross section of the cut ends of the guidewire assembly can help in orienting the cut ends, such as for insertion into a similarly-shaped opening of a connector.

Figure 3B:
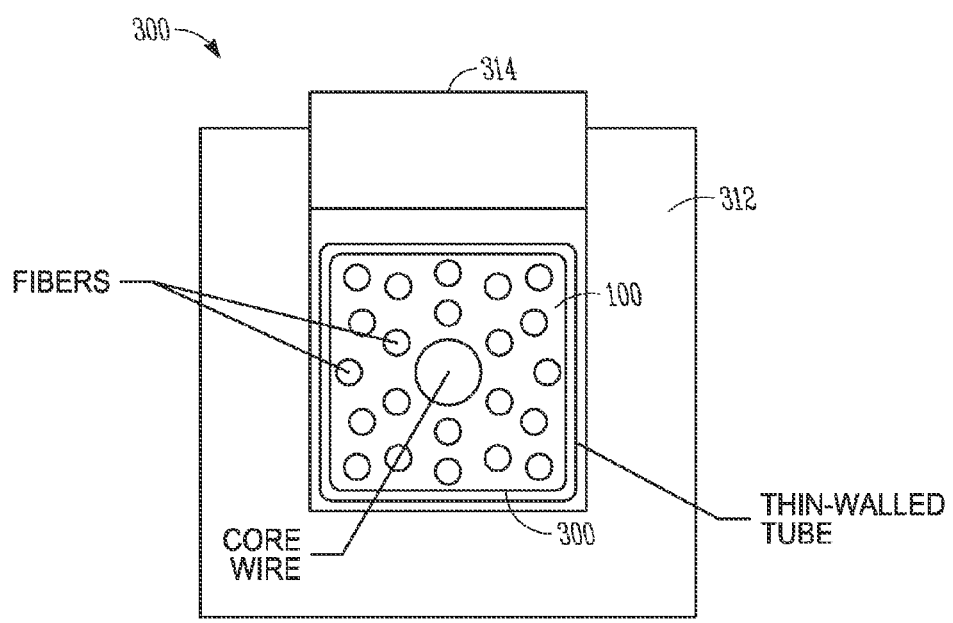
FIG. 3B shows an example of a connector that can be used for connecting the square cut ends of the guidewire assembly.

FIG. 3B shows an example of a connector 310 that can be used for connecting the square cut ends of the guidewire assembly 100. In an example, the connector 310 can include a ceramic channel 312 and a mating plug 314, such as to secure the cut ends of the guidewire assembly 100 together. In an example, the ceramic channel 312 and plug 314 can be produced with a tolerance within 1 micrometer. Fabricating such a connector, however, can involve obtaining similar manufacturing tolerances for the thin-walled tube 300 and the deformation process, which can be difficult or expensive.

Figures 4A, 4B:
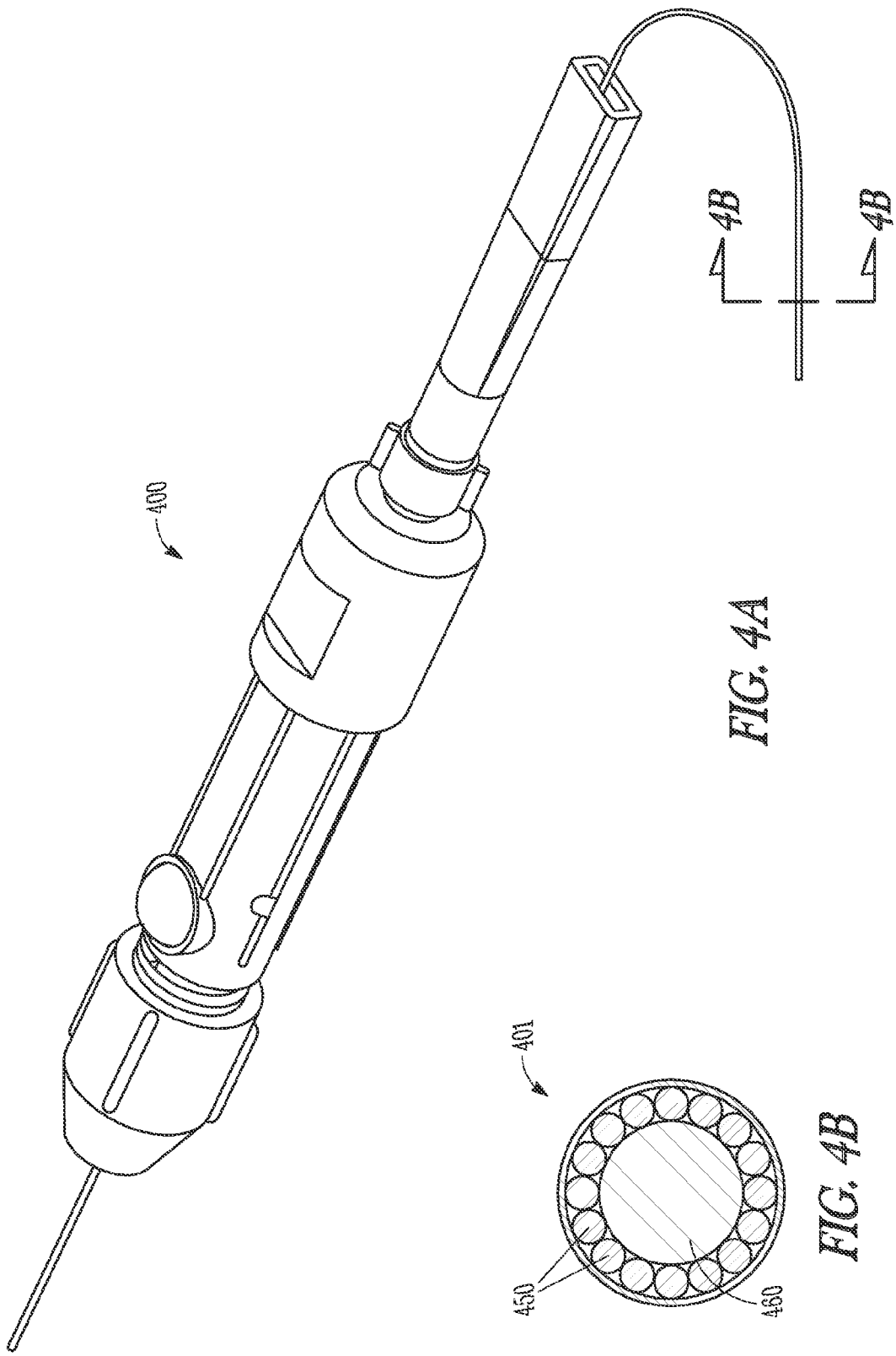
FIGS. 4A-4B show an example of the present optical imaging guidewire with a connector 400.

FIGS. 4A-4B show an example of the present optical imaging guidewire 401 with a connector 400. The example of FIG. 4B includes a cross section view of the guidewire assembly 401 taken along the cut-line shown in FIG. 4A. In this example, optical fibers 450 can be distributed around and affixed to the outer circumference of a core wire 460. When this guidewire assembly 401 of multiple (e.g., 32) optical fibers 450 around the core wire 460 is manufactured, the optical fibers 450 can be encapsulated along the length of the assembly such as in a protective coating, such as a plastic matrix. The placement of the optical fibers 450 around the core wire 460 can have a periodic, random, or other variation, such as due to equipment or manufacturing process variations. Although it can be possible to seat each of the optical fibers 450 accurately upon the core wire 460, there can also be an additional variation in core-to-cladding concentricity of the individual optical fibers 450, which can amount to 1 micrometer or more.

In an example, an individual probe can be made from a continuous length of assembled optical fibers 450 about a core wire 460. A connector 400 can be added to the probe portion of the guidewire assembly 401, such as to provide an easy, accurate, and fast connection of the probe portion of the guidewire assembly 401 to the lead portion of the guidewire assembly 401 in a sterile environment. The connector 400 can be configured to help a physician quickly and easily orient the mating cut ends of the guidewire assembly 401 so as to decrease or minimize optical energy loss or reflection, such as for better optical signal transmission. Because of manufacturing tolerances and the relatively small size of the optical fibers 450, improper orientation or alignment of the optical fibers 450 at a connector 400 could reduce the performance of the probe in transmitting optical signals between the external instrumentation and an internal sensor, transducer, or device, which can be located at or near the distal end of the probe portion.

Figure 5:
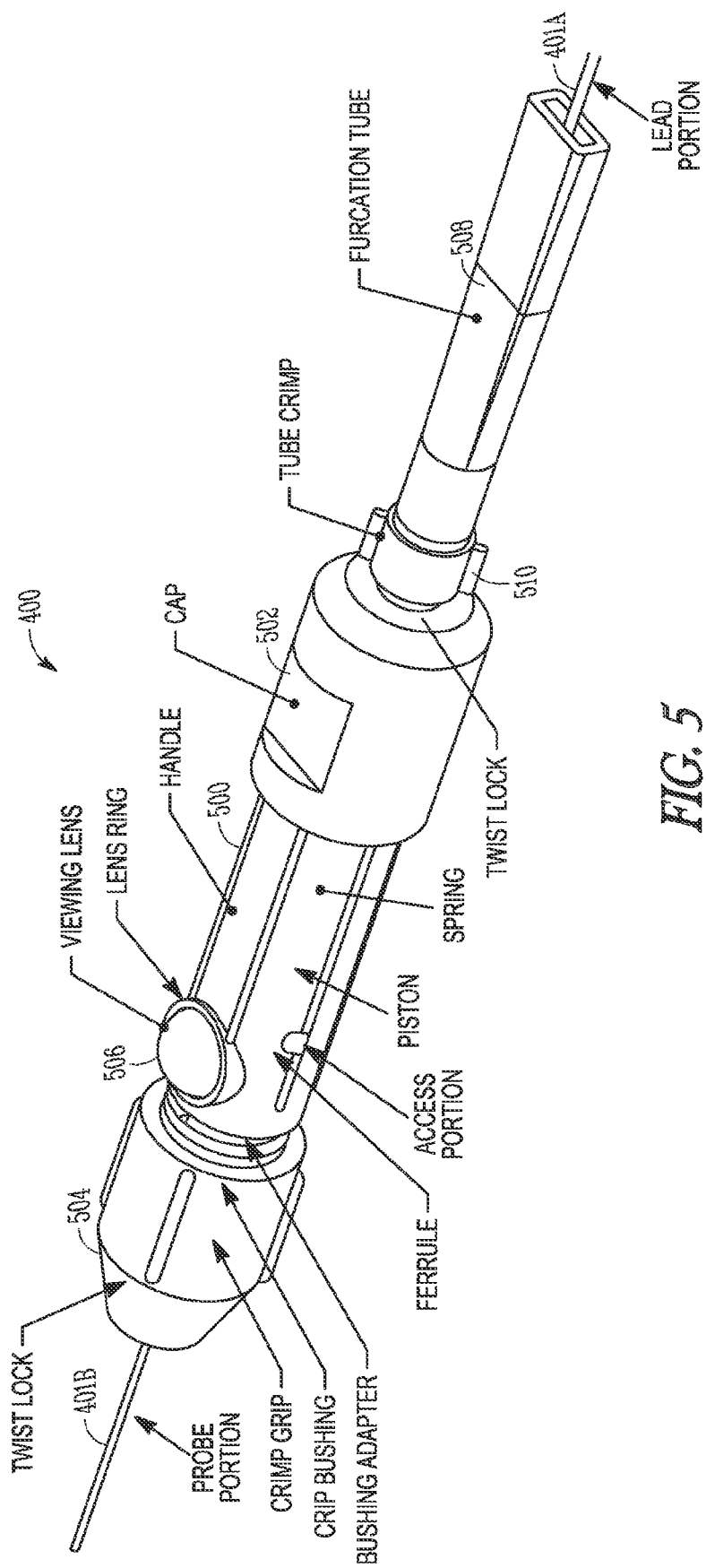
FIG. 5 shows an example of the present connector.

FIG. 5 shows an example of the present connector 400. In this example, the connector 400 can include a handle 500. The handle 500 can be connected to the lead portion 401A of a guidewire assembly 401, such as by using a compression cap 502. The handle 500 can be connected, such as with a crimp connection, to the probe portion 401B of the guidewire assembly 401, such as by using a twist lock assembly 504. The handle 500 can include a viewing port or a viewing lens 506 that can allow or magnify visualization of the area where the two ends of the guidewire assembly 401 meet within the connector 400. With the viewing lens 506, a physician or other user can more easily verify that the ends of the guidewire assembly 401 are abutted properly, such as with the correct orientation. In an example, a guiding reference light can also be provided, such as for helping indicate alignment of the probe portion 401B with the lead portion 401A using the lens port 506.

Figure 6A:
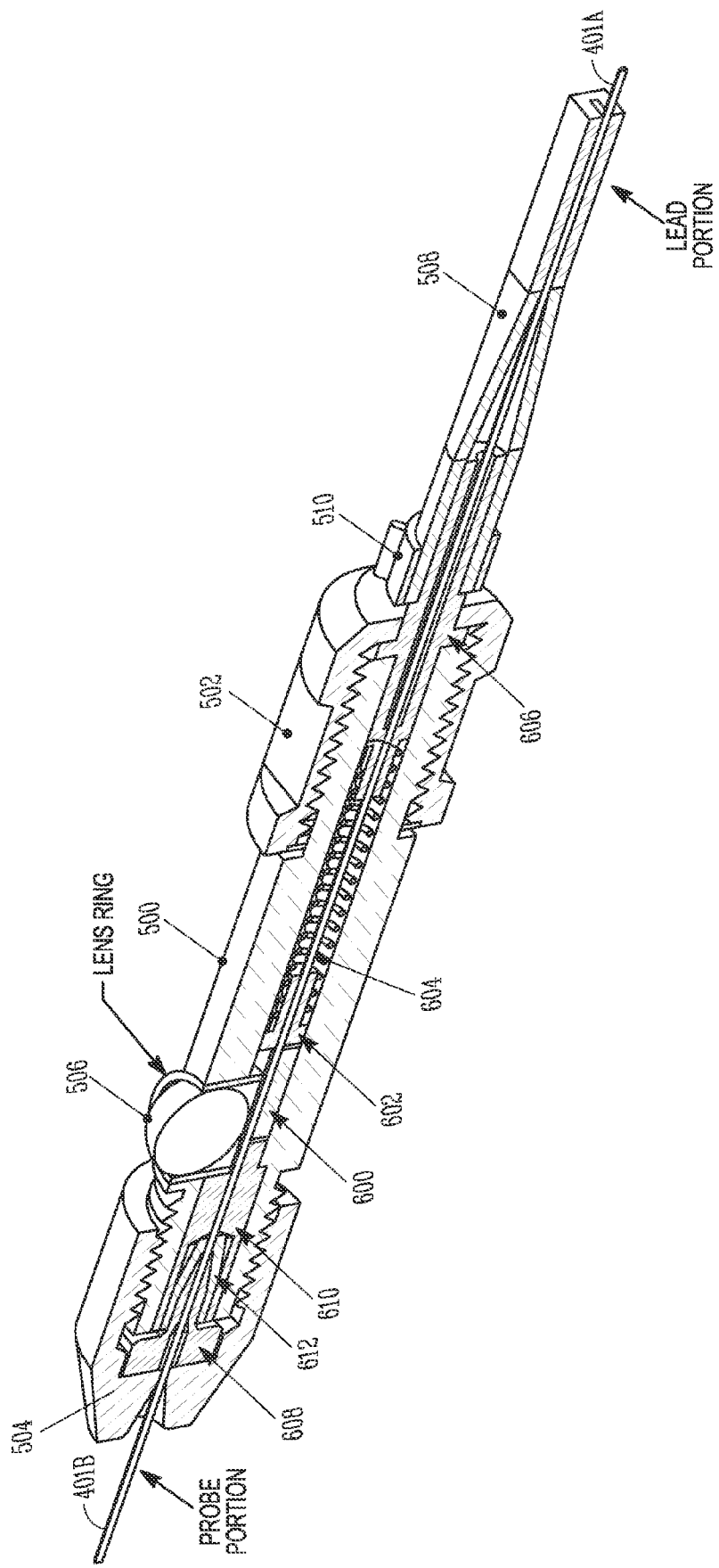
FIGS. 6A and 6B show examples of cutaway views of the present connector.
Figure 6B:
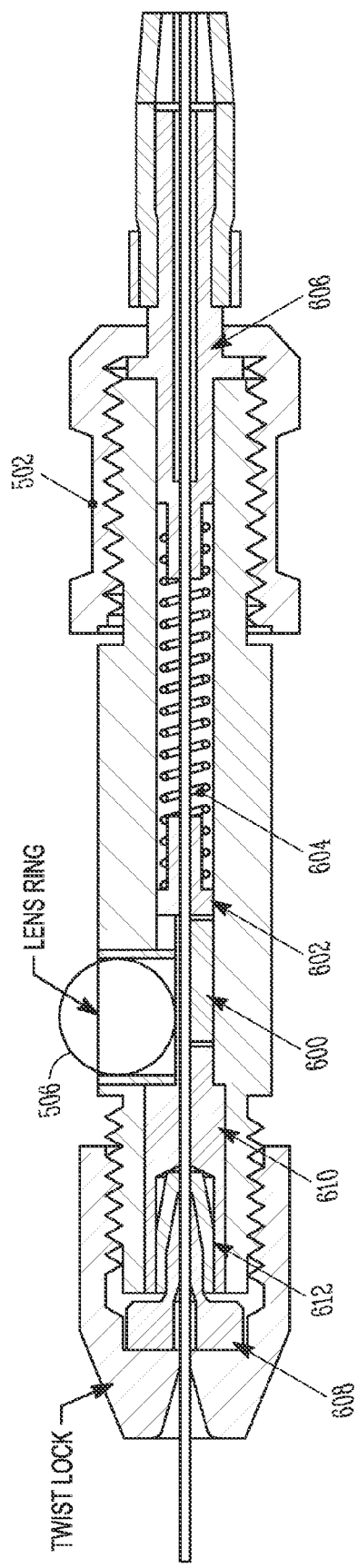

FIGS. 6A and 6B show examples of cutaway views of an example of the present connector 400. In this example, the connector 400 can include two sections. The first connector section can secure a lead portion 401A of a guidewire assembly 401. The second connector section can secure a probe portion 401B of the guidewire assembly 401.

In an example, the first connector section can include a handle 500, a compression cap 502, a furcation tube 508, and a tube crimp band 510. The handle 500 can enclose a ferrule 600, piston 602, spring 604, and tube adapter 606. The furcation tube 508 can be secured to the tube adapter 606, such as by using the tube crimp band 510. The furcation tube 508 can protect a section of the lead portion 401A of the guidewire assembly 401 that extends out from the connector 400. A portion of the tube adapter 606 can be held in place within the handle 500, such as by using the compression cap 502. In an example, the compression cap 502 can be threaded onto the handle 500. The compression cap 502 can engage a lip or other feature on the tube adapter 606, such that when the compression cap 502 is threaded onto the handle 500, it draws the tube adapter 606 into a lumen of the handle 500. A spring 604 can engage the tube adapter 606 and a piston 602. Biasing by the spring 604 and the compression cap 502 can help push the tube adapter 606 against the compression cap 502. Biasing by the spring 604 can also help push the piston 602 against the ferrule 600.

The ferrule 600 can be used to guide each portion of the guidewire assembly 401, to secure the lead portion 401A of the guidewire 401 within the connector 400, and to help orient the ends of the two portions of the guidewire assembly 401 such as during coupling by the connector 400.

In an example, the second connector section can include a threaded twist lock cap 504 and a crimp grip 608, such as to secure a section of the probe portion 401B of the guidewire assembly 401 within the connector 400. As the twist lock 504 is threaded onto the connector handle 500, the crimp grip 608 is compressed against a bushing adapter 610. This compresses the crimp grip 608 against the section of the probe portion 410B of the guidewire assembly 401 inserted into the connector 400, such as to hold the probe portion 410B in place.

Figure 7:
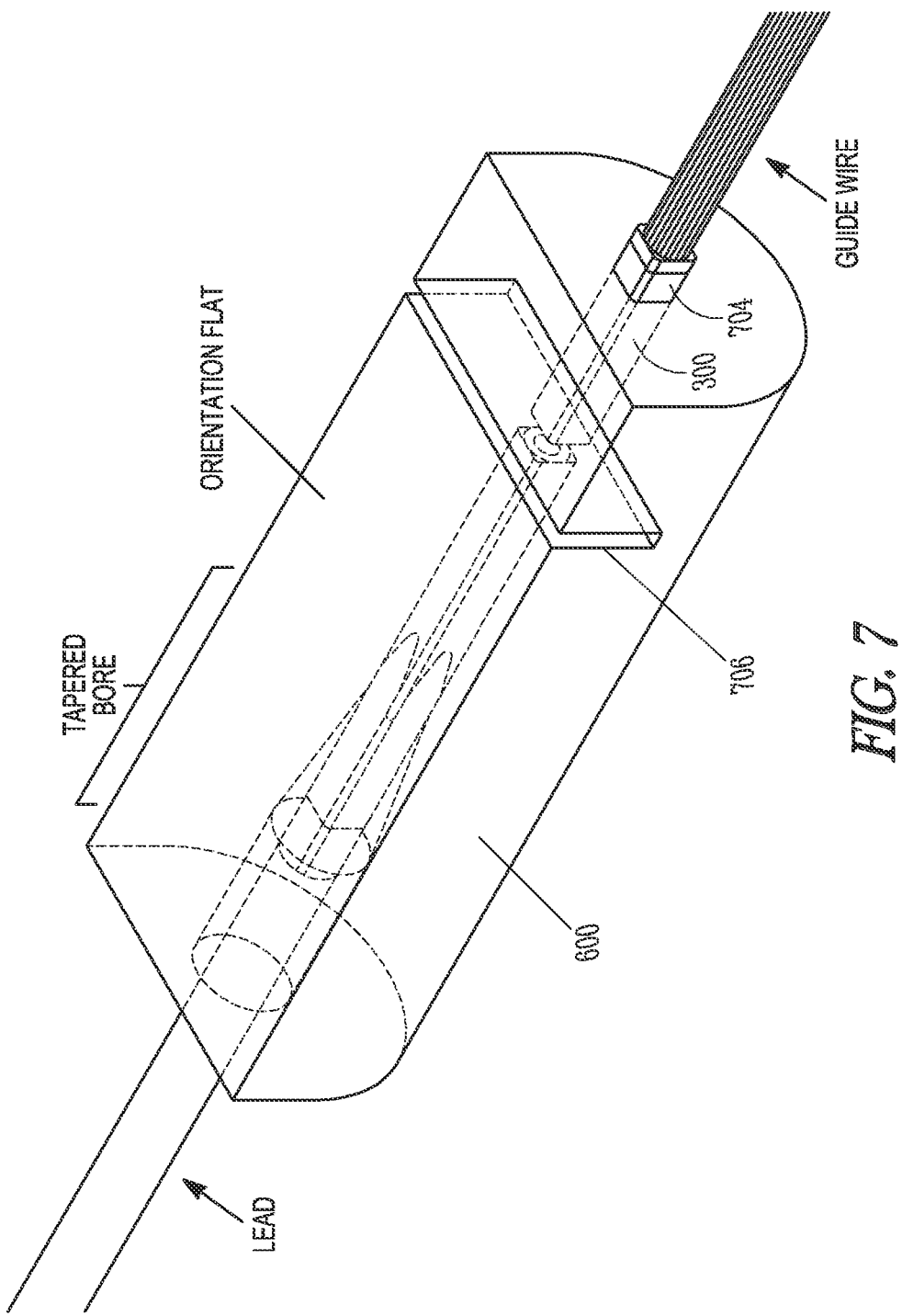
FIG. 7 shows an example of the present connector ferrule.

FIG. 7 shows an example of the present connector ferrule 600. In this example, a unitary section of an optical probe portion 410B and thin-walled tube 300 can pass through the ferrule 600. The ferrule 600 can include a lengthwise bore that can extend from one end of the ferrule 600 to an opposite second end 704 of the bore of the ferrule 600. A first end 702 of the bore can have a substantially circular cross-section. The shape of the bore cross-section can gradually change between the first end 702 and the second end 704, such that the second end 704 is a substantially square cross-section. The bore shape change within the ferrule 600 can also include a reduction in cross-sectional area as well as the change from a substantially circular cross-section to a substantially square cross-section.

A length of the guidewire 401 can be encompassed within a thin-walled malleable or otherwise deformable tube 300 within the ferrule 600. The guidewire 401 can be inserted through a length of the thin-walled malleable tube 300 before inserting both the guidewire 401 and the tube 300 together into the ferrule 600. Both the tube 300 and the guidewire 401 can have a substantially circular cross-section before insertion into the ferrule 600. In an example, the thin-walled tube 300 can include Phynox material made by Medelec. Other tube materials are also possible.

Figure 10:
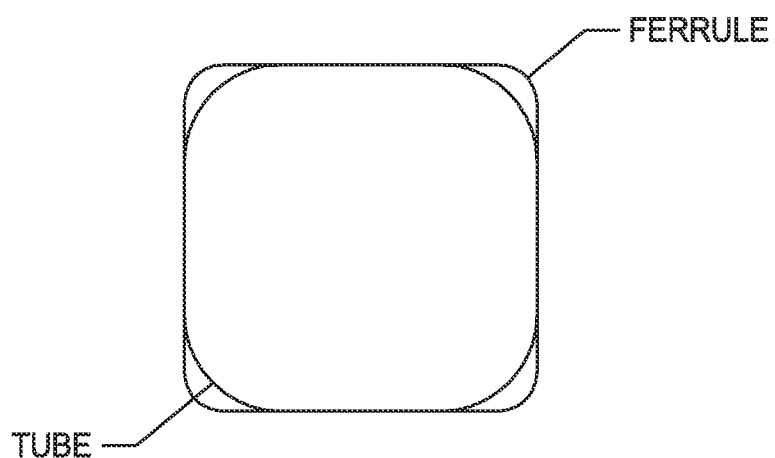
FIG. 10 shows an example of a cross section of a ferrule of the present connector with a deformed tube.
Figure 3A:
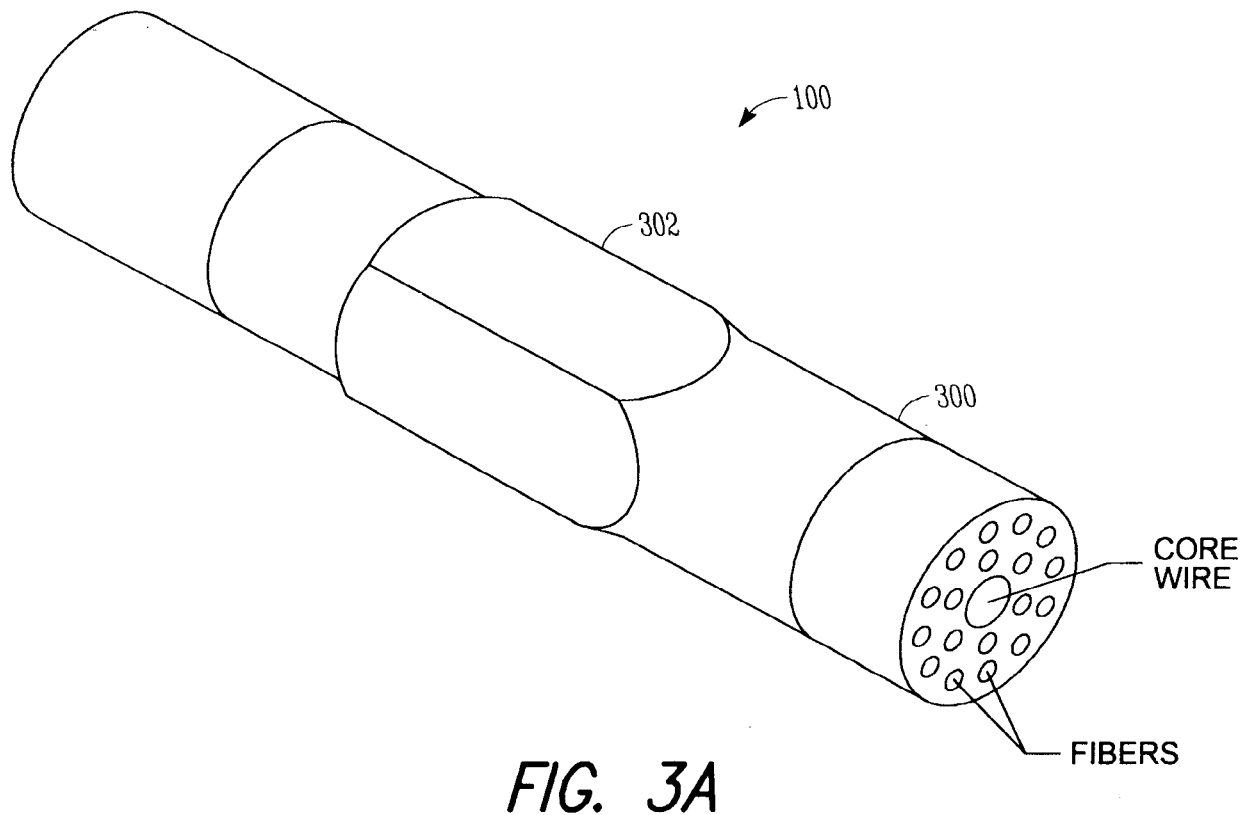
Figure 3B:
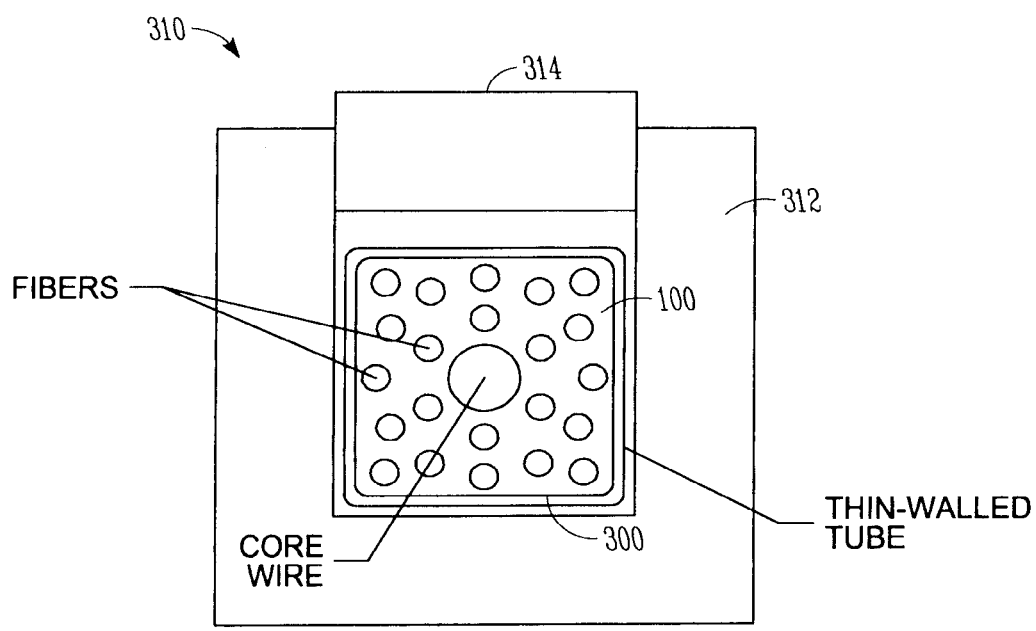

Upon inserting the guidewire 401 and the deformable tube 300 into the circular-bore end 702 of the ferrule 600 with enough force, the tube 300 deforms into a substantially square cross-section, which exits the square-bore end 704 of the ferrule 600. The guidewire assembly 401 can be cut into the two sections (e.g., as probe section 401B and a lead section 401A), such as by using a cutting blade. In an example, the guidewire assembly 401 can be cut while being supported in and by the ferrule 600. In an example, the cut can concurrently cut a slot 706 through the ferrule 600 and through the bore, such as at a location where the bore has a substantially non-circular (e.g., square) cross section. In an example, the two sections of the guidewire assembly 401 are packaged together, and the lead portion 401A is adapted to connect to external instrumentation, and the probe portion 401B is adapted to have its distal end inserted into a patient, such as through a lumen of a catheter. In an example, deforming the thin-walled tube 300 using the ferrule 600 can reduce or eliminate issues with manufacturing tolerances of the tube. For example, certain catheters have a guidewire lumen with a diameter measuring about 17 mils (1 mil=1/1000 of an inch). In an example, Phynox tubing can have a nominal diameter of just under 14 mils, subject to a manufacturing tolerance of +/−5 micrometers. Certain examples of economically available ferrules 600 can have a bore cross-sectional dimension having a manufacturing tolerance of +/−1 micrometer. In an example, the square bore portion of the ferrule 600 can include relatively sharp corners at each corner of the square. Such a relatively sharp corner can provide a place for the variation of the diameter of the tube 300 to be accommodated. The formed square section of the tube 300 can contact the side walls of the ferrule 600 such as to form a friction-fit, while the radii of the corners of the deformed tube 300 can be allowed to vary, thus taking up extra tube material. Deformation of a cylindrical tube 300, with a diameter of 14 mils, can create a square section of like perimeter. FIG. 10 shows an cross section example of a ferrule bore and deformed tube. In this example, the unoccupied areas near the corners of the ferrule bore shows that a given ferrule 600 can accommodate a range of tube 300 outer diameters.

In an example, the corner-to-corner cross-sectional dimension of the square can be only slightly larger than the undeformed diameter of the guidewire 401 enclosed by the deformable tube 300. For an initial nominal guidewire diameter of 14 mils, a thin walled-tube 300 having an outer dimension that can vary from about 343 µm to about 353 µm can be accommodated with a ferrule 600 having a square bore cross-section side dimension of about 290 µm. For a larger diameter tube 300 of about 353 µm, the resulting substantially square profile can have an effective radius of about 385 µm, or about 15 mils, at the connector end of the probe portion 401B of the guidewire assembly 401 including corner radiuses of about 30 µm. For a smaller diameter tube 300 of about 343 µm, the resulting substantially square profile can have an effective radius of about 370 µm at the connector end of the probe portion 401B of the guidewire assembly 401 including corner radiuses of about 48 µm. In an example, the length of the slightly larger diameter can be very short, for example, only a millimeter or so. Generally, the guidewire lumens of therapeutic catheters are manufactured with lumens of about 17 mils. Therefore, even though the square section has a maximum diameter slightly larger than 14 mils, it is only for a short section of its length, which can easily be accommodated and passed by the guidewire lumen of a therapeutic catheter. Also, the square section will exit the proximal end of the therapeutic catheter before the distal end is fully advanced to the therapy site, thereby allowing fairly easy tracking of the therapeutic catheter over the guidewire.

As discussed above, the two portions of the guidewire assembly 401 (e.g., probe portion 401B and lead portion 401A) can be formed by cutting a unitary guidewire 401 at a location at which the guidewire 401 is within a thin-walled tube 300, both of which are inserted into the ferrule 600. The cut can be made at the same time as creating a slot 706 in the ferrule 600. The slot 706 can be located across the square cross-sectional bore portion of the ferrule 600, such as shown in the example of FIG. 7. Making the cut using the ferrule 600 allows the ferrule 600 to firmly support the guidewire assembly 401 during the cut, which can help obtain a clean cut. In an example, the slot 706 can be about 100 micrometers wide. Cutting the guidewire assembly 401 through the ferrule 600 can create a clean cut slot 706, can enable further polishing if desired, and can leave square cross sections at the cut ends of the two guidewire assembly portions. Provided that the core wire and optical fibers travel through the tube 300 in a substantially parallel and straight manner, these cross sections can be nearly mirror images of each other. The four sided square cross section of each guidewire portion's cut end can help reduce the chance of misalignment or improper orientation of corresponding optical fibers when the cut ends are recoupled together in the connector 400. In an example, the chance of misalignment and misorientation of the probe section 401B and lead section 401A of the guidewire assembly 401 can be further reduced by one or more additional precautions, such as by visibly marking a properly-mated side of the deformed tube 300 at both sides of the cut, or by cutting the guidewire assembly 401 at an oblique angle, such that each end has a bevel that mates with a bevel of the other end when properly oriented.

In an example, at the lead portion 401B, the tube 300 can be secured into the ferrule 600 before cutting the guidewire 401 and ferrule 600. In an example, the lead portion of the guidewire 401 can be secured to the ferrule 600, such as by applying adhesive or epoxy to secure the guidewire 401 in the thin-walled tube 300 and to secure the tube 300 to the ferrule 600 such that upon cutting the guidewire 401, the lead portion 401B remains secured to the ferrule 600. Upon completing the cut, a cloth ribbon or other cleaning or polishing component can be drawn through the ferrule slot 706, such as to allow each cut end of the guidewire assembly 401 to be cleaned or polished (see, e.g., FIG. 9). In practice, the cut ends of the guidewire assembly 401 can often be exposed to blood, moisture, or other contaminants that could interfere with optical communication between the cut ends if not cleaned before the cut ends are coupled together by abutment. In an example, the connector 400 can include a cleaning cloth ribbon or other mechanism such as to allow a user to easily clean the cut ends of each guidewire assembly 401 portion just before completing the coupling by abutment In an example, deforming the tube 300 and enclosed guidewire assembly 401 can displace or otherwise disrupt the core wire or surrounding optical fibers. In an example, after the guidewire assembly 401 is deformed in the ferrule 600, but before cutting the guidewire assembly 401, the guidewire assembly 401 can be injected with a hardenable material, such as to help stabilize the position of the optical fibers and the core wire. After cutting the guidewire assembly 401, the newly cut ends are substantially mirror images of each other, even if the deformation significantly displaces the optical fiber or core wire components of the guidewire assembly 401. In an example, deforming a cylindrical tube 300 having about a 350 µm outer diameter can result in a four-sided square cross-sectional profile with each side of the square measuring in a range of about 175 µm to about 210 µm. In an example, the radii of the corners is in a range of about 40 µm to about 60 µm. Our experiments indicate that even though the maximum cross-sectional dimension of the deformed tube 300 is slightly larger than the outer diameter of the un-deformed tube 300, the deformed portion of the tube 300 easily passes through a typical catheter having a lumen capable of accommodating the cylindrical outer diameter of the un-deformed tube.

In an example, the twist lock cap 504 can be loosened such as to allow removal of the probe portion 401B of the guidewire assembly 401 from the connector 400. The twist-lock cap 504 need not be removed from the handle 500 to allow removal of the end of the probe portion 401B from the connector 400. To re-couple the probe portion 401B to the lead portion 401A, the cut end of the probe portion 401B can be inserted through the opening in the twist-lock cap 504 into the ferrule 600. In an example, the twist-lock cap 504, the crimp grip 608, and the ferrule 600 can include tapered or funneled openings, such as to help guide the end of the probe portion 401B into the connector 400. Tightening the twist-lock cap 504 can help secure the end of the probe portion 401B of the guidewire assembly 401 within the connector 400.

In an example, a cleaning component can be inserted temporarily in the slot 706 of the ferrule 600, such as before tightening the twist lock cap 504, the compression cap 502, or both. After cleaning the mating ends of the guidewire assembly 401 portions, the ends are tightened to secure the coupling therebetween by abutment. In an example, tightening the compression cap 502 can compress a spring 604 within the handle 500. The spring 604 can push against a piston 602, which, in turn, can push against the ferrule 600. If a gap exists between the cut ends of the guidewire assembly 401 portions, the spring 604 can provide a biasing force that can move the ferrule 600 and lead portion 401B such that the ends butt together to provide good optical coupling therebetween.

Figure 8:
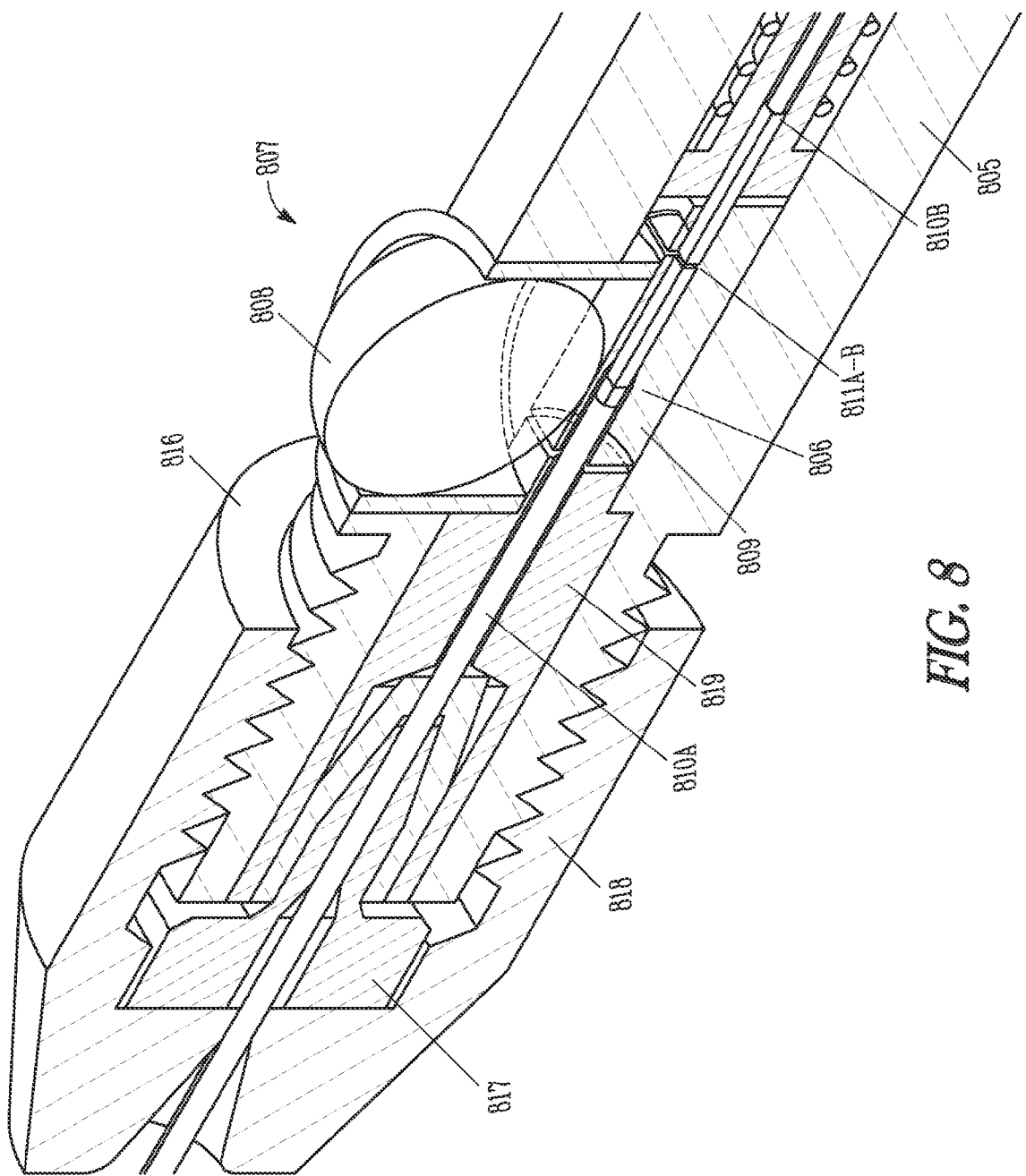
FIG. 8 is a cutaway view of an example of the present connector.

FIG. 8 is a cutaway view of an example of the present connector 400. The view of FIG. 8 includes an area of the connector near the ferrule 600, 809. In this example, the connector 400 can include a twist lock cap 504, 816 having internal threads such that it can be threaded onto external threads of a handle 500, 805. The twist lock cap 504, 816 can include a crimp grip 608, 817, a portion of which can be received and engaged in a crimp bushing 612, 818. The crimp bushing 612, 818 can be received and engaged into a bushing adapter 610, 819 within the connector handle 500, 805. The crimp grip 608, 817 can secure a cylindrical portion of a thin-walled tube 300 enclosing an end region of the probe portion 401B of the guidewire assembly 401. The tube and end region of the probe portion 401B, 810A can extend through longitudinal lumens of the crimp grip 608, 817, crimp bushing 612, 818, and the bushing adapter 610, 819, into a lumen of the ferrule 600, 809. The cross-sectional profile of a portion of the tube 300 is re-shaped during such insertion, such as to substantially match the square cross-sectional ferrule bore profile near the end 704 of the probe portion 401B 811A. During coupling or re-coupling using the connector 400, the end of the probe portion 401B can extend through the ferrule 600, 809 until the end of the probe portion 401B, 811A butts against the corresponding end 811B of the lead portion 401A, 810B of the guidewire assembly 401, such as at a location that is at or near the cut slot 706 across the lumen or bore of the ferrule 600, 809.

In an example, the handle 500, 805 can include an viewing port or other opening 807, which can include a lens ring and a light-refracting viewing lens 506, 880. The viewing lens 506, 880 and the opening 807 can allow a user to visually verify proper abutting coupling of the two guidewire sections, including their proper orientation at a coupling location that can be at or near the cut slot 706 of the ferrule 600, 809. In an example, the lens 506, 880 can significantly magnify the cut slot 706 area for allowing easier visual verification. In an example, an antireflective surface coating can be used at the beveled ends 811A-B of the guidewire portions, or a refractive index matching fluid can be used between the beveled ends 811A-B, such as to help improve the amount of light coupled between the ends of the optical fibers of the respective probe portion 401B, 810A and the external instrumentation lead portion 401A, 810B. The index matching fluid can have substantially the same refractive index as the optical fiber at the desired wavelength of light used. It can reduce or eliminate the likelihood of a fiber-air-fiber interface, which could cause undesirable reflections of light at the junction between the probe portion 401B, 810A and the external instrumentation portion 810B. A fiber-air-fiber interface can occur if the beveled ends 811A-B do not butt against each other in direct mechanical contact even though otherwise in optical alignment.

In an example, the external instrumentation lead portion 401A, 810B can be directly or indirectly secured to the connector handle 400, 805, such as by using an adhesive or other suitable technique, such as to position the tip of the beveled end 811B within a viewable perimeter of a view hole or port 807. This allows the tip to be oriented toward a view lens 506, 880 in the view hole 807. The lens 506, 880 can use one or more antireflective surface coatings, such as to increase light transmission through the lens 506, 880. The probe portion 401B, 810A can be inserted into the connector handle 500, 805. This can be helped by a beveled or otherwise tapered ferrule internal lumen surface 806, which can form a funnel-like structure, such as to reduce or minimize any potential damage to the beveled end 811A of the probe portion 401B, 810A when inserting it into the ferrule 600, 809. Beveling or tapering of a lumen can also help orient an end region of the external instrumentation lead portion 401A, 810B such as during insertion into the connector 400.

In an example, for aligning the beveled ends 811A-B, visible light (e.g., red light emitted from a diode, etc.) can be transmitted from the instrumentation lead portion 401A, 810B while the probe portion 401B, 810A is being inserted into the connector handle 500, 805. Such visible light exiting an optical fiber at the beveled end 811B of the external instrumentation lead 401A, 810B can be reflected by at least one optical fiber at the beveled end 811A of the probe portion 401B, 810A, before abutment, such as through the view lens 506, 880. Before abutment, a user looking at the view lens 506, 880 will observe maximum intensity of the reflected light when the probe portion 401B, 810A is properly oriented and aligned with respect to the external instrumentation lead portion 401A, 810B. In another example, light striking the lens 506, 880 can be coupled to a photodetector and, before end-abutment, the resulting signal from the photodetector can be similarly monitored and used for manually or automatically (e.g., robotically) aligning the beveled ends 811A-B. In an example, the lens 506, 880 can be omitted, and light propagating through the view hole 807 can instead be coupled directly to an external photodetector. The resulting photodetector output signal can be used for manually or automatically aligning the beveled ends 811A-B. In an example, the alignment light can be coupled to an external photodetector by a lens 506, 880, which need not be secured to the handle 500. In an example, the circumferential surface of the view hole 807 can be polished or coated with a reflective film or otherwise configured to help improve surface reflectivity of the light used for aligning the beveled ends 811A-B.

During insertion of the probe portion 401B, 810A into the handle 805, the probe portion 401B, 810A can be rotated, such as to obtain maximum alignment light reflected toward the view lens 506, 880 from the beveled end 811B of the external instrumentation lead portion 401A, 810B. When such alignment has been obtained, the probe portion 401B, 810A and external instrumentation lead portion 401A, 810B can be butted into direct mechanical contact. Before such abutment, more light is reflected toward the view hole 807 when the optical fibers of the probe portion 401B, 810A and the external instrumentation lead portion 401A, 810B are best aligned. Then, when the beveled ends 811A-B of the probe portion 401B, 810A and the lead portion 401A, 810B are abutted in mechanical contact with each other, such abutment can be obtained with maximum optical alignment, such that substantially all of the alignment light transmitted from external instrumentation lead portion 401A, 810B is optically coupled into the probe portion 401B, 810A, leaving no light for reflection towards the view hole 807. As discussed above, index matching fluid may be used between the beveled ends 811A-B, such as to help improve light coupling between the beveled ends 811A-B. The end of the probe portion 401B, 810A can then be secured to the connector handle 500, 805, such as by a twist lock cap 504, 816 and the crimp assembly.

In the example of FIG. 8, such alignment of the probe portion 401B, 810A and the external instrumentation lead portion 401A, 810B using the view hole 807 is generally possible when the angle of the beveled end 811B is less than the critical angle for total internal reflection.

Figure 9A:
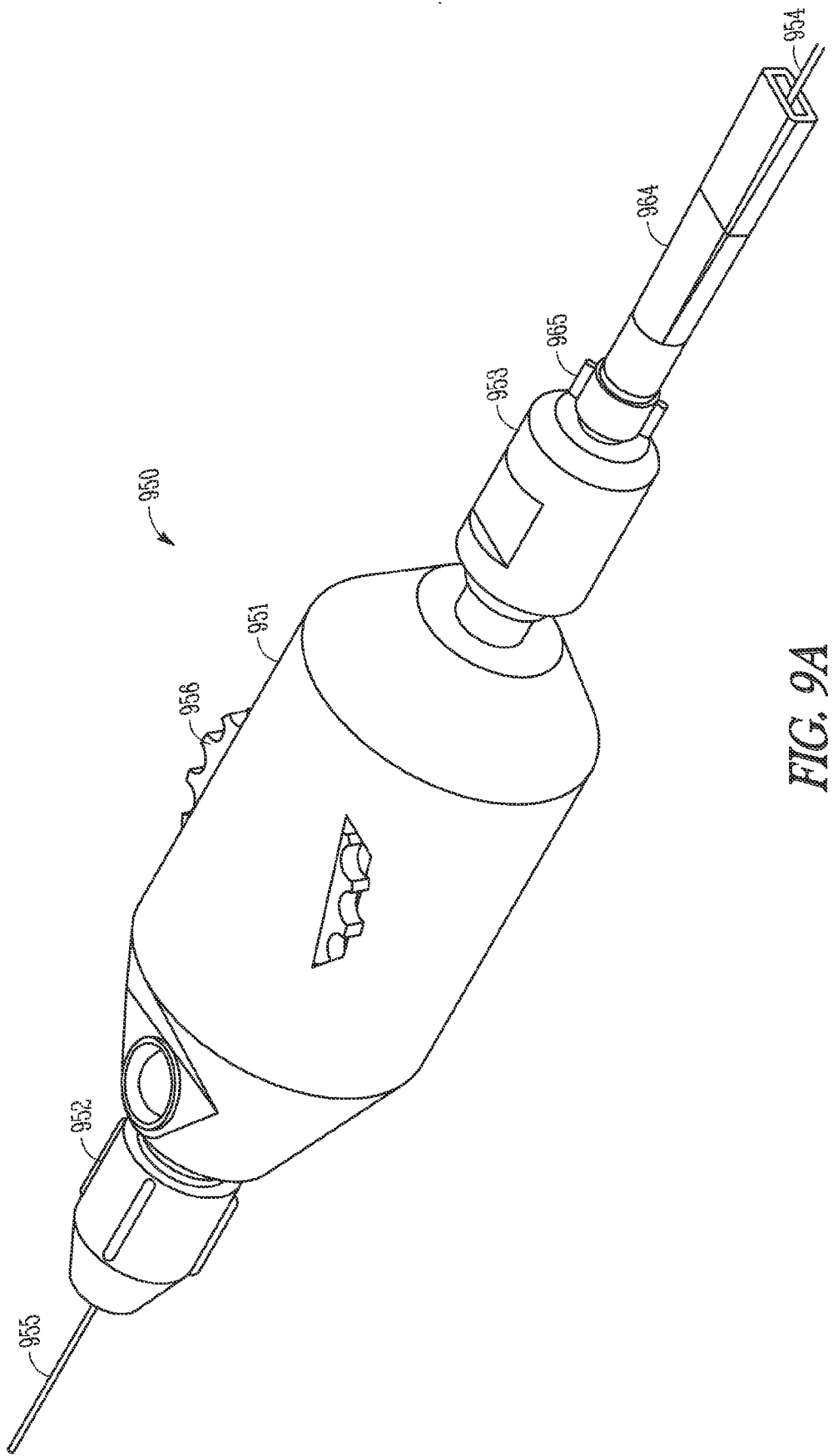
FIG. 9A-9C show an example of the present connector with an integrated cleaning mechanism.
Figure 9B:
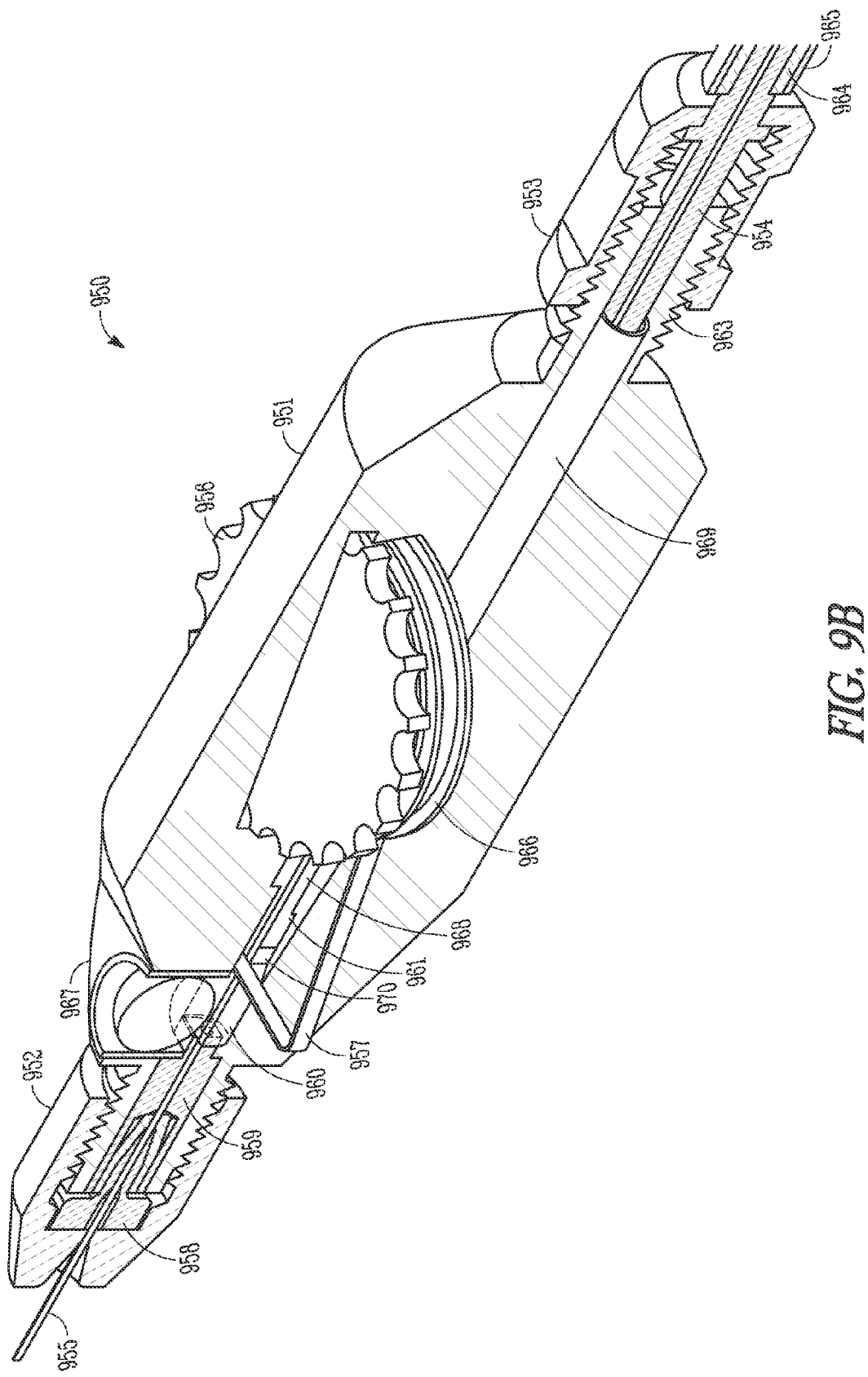
Figure 9C:
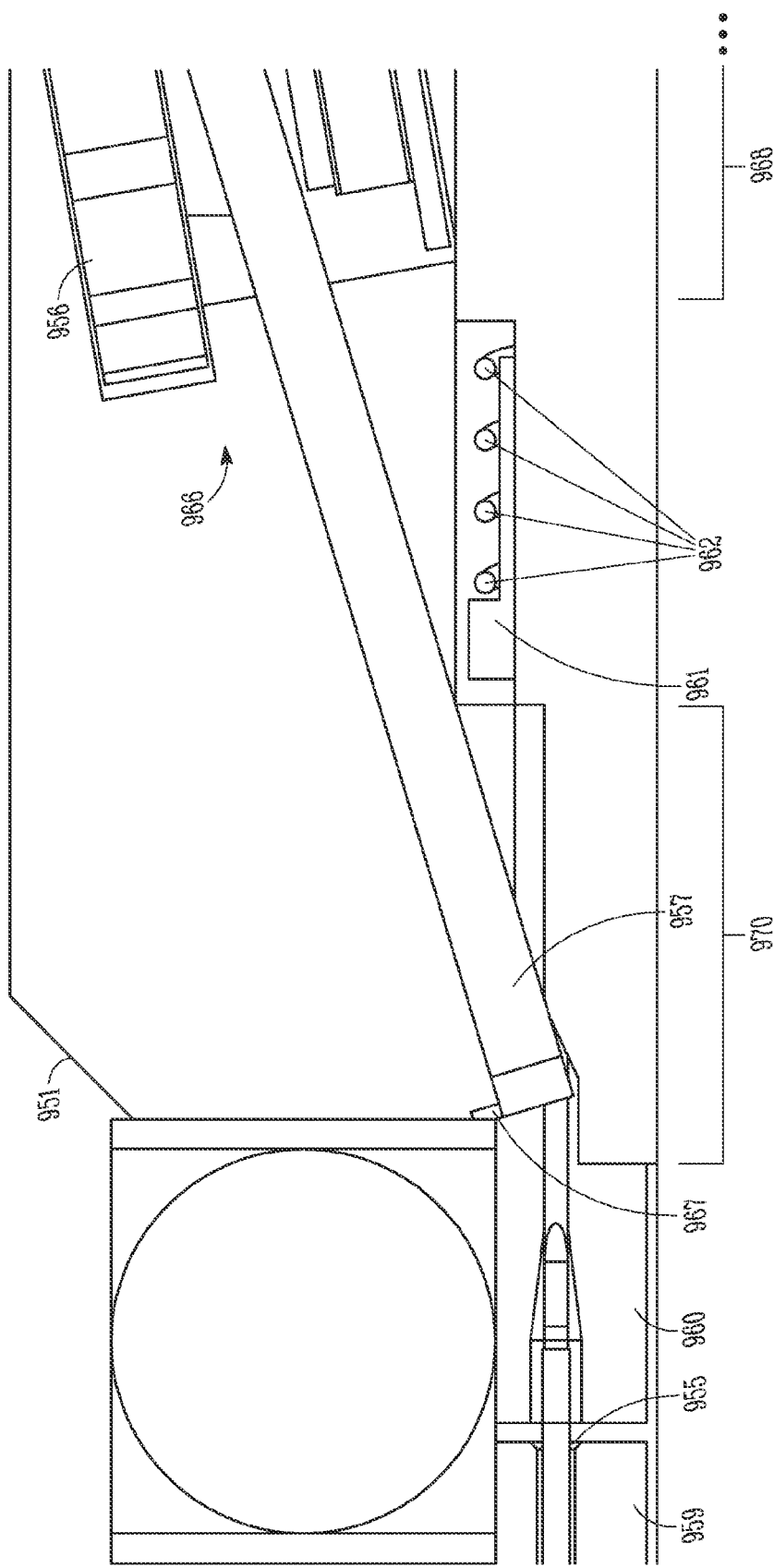

FIG. 9A-C show an example of the present connector with an example of an integrated cleaning mechanism. The view of FIG. 9A shows the assembled connector 950 coupling an optical guidewire assembly. The connector 950 can include a handle 951 with a twist-lock cap 952 assembled to one end and a compression cap 953 assembled to the other end. The compression cap 953 can also couple a furcation tube to the handle 951 such as to protect the lead portion 401A, 954 of the guidewire assembly near the connector 950. The handle 951 can include a cleaning mechanism. The cleaning mechanism can be used to remove debris from the ends of the guidewire assembly before the lead 954 and probe 955 portions of the guidewire assembly are coupled together within the connector 950. Debris, such as blood and other bodily fluids, trapped between the ends of the lead 954 and probe 955 portion of the guidewire assembly can reduce the performance of the optical guidewire. In a surgical environment, reduced performance of the optical guidewire can create unnecessary delay in treating a patient. In FIG. 9A, a portion of a knob 956 of the cleaning mechanism is visible. Cleaning the ends of the probe 955 and lead 954 portions of the guidewire assembly can include rotating the knob 956 to wipe a cleaning strip material 957 across the ends of the lead and probe portions of the guidewire assembly.

FIG. 9B shows an example of cutaway view of an example of the present connector with an example of a cleaning mechanism. When reconnecting the guide wire assembly, the probe portion 955 can be inserted into the connector through the twist lock cap 952, a crimp grip 958 and a bushing adapter 959 into the connector ferrule 960. The twist lock cap 952 and crimp grip 958 can include funneled or like openings such as to steer the end of the probe portion 955 through the connector components.

The ferrule 960 can also include a funneled opening to receive the end of the probe portion 955 of the guidewire assembly. The end of lead portion 954 of the guidewire assembly can be fastened within the ferrule 960 and can extend out of the handle, such as through a piston 961, spring 962 (FIG. 9C), tube adapter 963, the compression cap 953, a furcation tube 964, and tube crimp band 965 (partially shown). The ferrule 960 can include a slot 967, which can be created when cutting the guidewire to form the lead 954 and probe 955 portions of the guidewire assembly. In FIG. 9B, cleaning strip material 957 can be positioned through the slot of the ferrule 960. The cleaning strip material 957 can be fastened to a reel 966 with a knob 956. Upon rotating the knob 956, the cleaning strip material 957 moves through the slot 967 in the ferrule 960. The movement of the cleaning strip material 957 can wipe the end of the lead portion 954 of the guide wire assembly fastened in the ferrule. This can remove debris that can interfere with the performance of the guidewire assembly. If a probe portion 955 is inserted into the connector 950, the movement of the cleaning strip material 957 can wipe the end of the probe portion 955. This can remove debris that can interfere with the performance of the guidewire assembly. The reel 966 can include two spools. One end of the cleaning strip material 957 can be fastened to one spool and the other end of the cleaning strip material 957 can be fastened to the other spool.

The illustrated connector example of FIG. 9B shows an actuator tube 968 such as to adjust the position of the cleaning strip material 957 perpendicular to the motion of the cleaning strip material using the knob 956 of the reel 966. The actuator tube 968 can cause the cleaning strip material 957 to be moved into and out of the ferrule slot 967, at least partially, such that the ends of the probe portion 955 and lead portion 954 can be abutted to each other. In an example, the actuator tube 968 can be influenced by the compression cap 953 through the tube adapter 963. Tightening the compression cap 953 can cause the tube adapter 963 and actuator tube 968 to move into the handle 951. Releasing the compression cap 953 can cause the tube adapter 963 and actuator tube 968 to withdraw from the handle 951. The actuator tube can include a tube portion 969 enclosing the spring 962 and piston 961, and a profiled portion 970 configured to move the cleaning strip material 957 in to and out of the ferrule slot 967.

FIG. 9C shows an example of a cutaway detail of an example of the present connector with an example of a cleaning mechanism. FIG. 9C shows the profile portion 970 of the actuator tube 968 that can be used for moving the cleaning strip material 957 into and out of the ferrule slot 967. In the illustrated state, the actuator tube 968 and the cleaning strip material 957 are positioned for cleaning the ends of the probe 955 and lead 954 portions of the guide wire assembly. Upon cleaning the ends of the guidewire assembly, the actuator tube 968 can be used to remove the cleaning strip material 957 from the gap between the ends of the guidewire assembly to compete the connection. Tightening the compression cap 953 causes the tube adapter 963 to push the actuator tube 968 further into the handle 951. The profile portion 970 of the actuator tube 968 can use the actuator tube walls to form a ramped fork. Upon moving the actuator tube 968 further into the handle 951 the ramps integrated into the profile portion 970 can withdraw the cleaning strip material 957 out of the slot area 967 of the ferrule such that the ends of the guidewire assembly can be abutted. In some examples, removing the cleaning strip material 957 from the gap between the ends of the guidewire assembly can allow the spring 962 and piston 957 to move the ferrule 960 and attached lead end of the guidewire assembly toward the probe end, such as to complete the coupling of the guidewire assembly. In some examples, additional tightening of the compression cap 953 can bias the spring 962 and cause the piston 961 to move the ferrule 960 and lead portion of the guidewire toward the end of the probe portion, such as to complete the coupling.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An apparatus comprising:
   an elongated optical guidewire assembly, comprising a longitudinal core wire and a plurality of longitudinal optical fibers arranged about the core wire and a deformable tube having an outer diameter and enclosing a portion of the plurality of optical fibers, the optical guidewire assembly including a cut through a deformed portion of the tube at an oblique angle, wherein the cut provides first and second portions that are configured to respectively provide oblique angle beveled first and second ends that are mirror images of each other, wherein the first and second ends are configured to be mechanically self-aligned and coupled together and optically coupled together at the respective first and second ends comprising respective first and second cross-sectional profiles; and
   a connector comprising a bore including first and second bore ends, the first bore end comprising a substantially circular cross-sectional profile and the second bore end comprising a substantially non-circular cross-sectional profile, wherein the bore is configured to receive the optical guidewire assembly at the first bore end and configured to deform the optical guidewire assembly at the second bore end such that the first and second ends of the optical guidewire assembly are deformed into a substantially non-circular profile and located between the first and second bore ends.

2. The apparatus of claim 1, wherein the tube is configured to be deformed in the bore and the tube is separated into a first tube portion and a second tube portion, wherein the first tube portion encloses the first portion of the guidewire assembly at or near the first end of the first portion of the guidewire assembly, and wherein the second tube portion encloses the second portion of the guidewire assembly at or near the second end of the second portion of the guidewire assembly.

3. The apparatus of claim 2, wherein the connector includes a ferrule including at least a portion of the bore.

4. The apparatus of claim 3, wherein the second tube portion and the second end of the guidewire assembly are attached to the ferrule at a location within the bore near the second bore end.

5. The apparatus of claim 3, wherein the connector comprises a handle including the ferrule.

6. The apparatus of claim 5, wherein the connector comprises a compression link connected to the handle at a first end and configured to apply a longitudinal bias force to the ferrule and to bias the oblique angle beveled first and second ends against each other.

7. The apparatus of claim 6, wherein the second portion of the tube and the second end of the second portion of the guidewire assembly are attached to the ferrule within the bore at or near the second bore end.

8. The apparatus of claim 5, comprising a cleaning element configured to pass through a slot in the ferrule for cleaning the first and second ends of the first and second portions of the guidewire assembly.

9. The apparatus of claim 1, wherein an outer diameter of the tube is between about 343 micrometers (µm) and about 353 µm.

10. The apparatus of claim 1, wherein the deformed portion of the tube includes a substantially square cross-section.

11. The apparatus of claim 10, wherein a corner-to-corner cross-sectional dimension of the substantially square cross-section is larger than an un-deformed cross-sectional portion of the longitudinal optical fibers enclosed by the tube.

12. The apparatus of claim 1, comprising:
   a ferrule, including a bore with a circular cross section at a first end and a non-circular cross-section at the second end;
   wherein the deformed portion of the tube is deformed to a shape that is in defined by an interior portion of the bore of the ferrule; and
   wherein the deformed portion of the tube is sized and shaped to pass through a guidewire lumen of a catheter.

13. The apparatus of claim 1, comprising:
   a ferrule, including a bore with a circular cross section at a first end and a non-circular cross-section at the second end;
   wherein the deformed portion of the tube is deformed to a shape that is in defined by an interior portion of the bore of the ferrule; and
   wherein the elongated optical guidewire assembly includes an optoacoustic imaging probe portion, proximally terminated at the oblique angle beveled first end, and a system connector lead portion, proximally terminated at the oblique angle beveled second end.

14. The apparatus of claim 1, comprising:
a ferrule, including a bore with a circular cross section at a first end and a square cross-section at the second end; and
wherein the deformed portion of the tube is deformed to a shape that is in defined by an interior portion of the bore of the ferrule.

15. The apparatus of claim 1, comprising:
a ferrule, including a bore with a circular cross section at a first end and a non-circular cross-section at the second end;
wherein the deformed portion of the tube is deformed to a shape that is in defined by an interior portion of the bore of the ferrule; and
wherein the ferrule includes a slot defining the oblique angle, the slot sized and shaped to accept at least a portion of a cutting device within the slot.

16. The apparatus of claim 1, wherein the optical fibers are secured within the deformable tube using a flowable and hardenable substance.

17. An apparatus comprising:
an elongated optical guidewire assembly, comprising a longitudinal core wire and a plurality of longitudinal optical fibers arranged about the core wire and a deformable tube having an outer diameter and enclosing a portion of the plurality of optical fibers, the optical guidewire assembly including a cut through a deformed portion of the tube at an oblique angle, wherein the cut provides first and second portions that are configured to respectively provide oblique angle beveled first and second ends that are mirror images of each other, wherein the first and second ends are configured to be mechanically self-aligned and coupled together and optically coupled together at the respective first and second ends comprising respective first and second cross-sectional profiles;
a connector comprising a bore including first and second bore ends, the first bore end comprising a substantially circular cross-sectional profile and the second bore end comprising a substantially non-circular cross-sectional profile, wherein the bore is configured to receive the optical guidewire assembly at the first bore end and configured to deform the optical guidewire assembly at the second bore end such that the first and second ends of the optical guidewire assembly are deformed into a substantially non-circular profile and located between the first and second bore ends, wherein the connector comprises a compression link connected to the handle at a first end and configured to apply a longitudinal bias force to the ferrule and to bias the oblique angle beveled first and second ends against each other; and
a ferrule, including a bore with a circular cross section at a first end and a square cross-section at the second end, the ferrule including a slot defining the oblique angle, the slot sized and shaped to accept at least a portion of a cutting device within the slot, and wherein:
the deformed portion of the tube is deformed to a shape that is in defined by an interior portion of the bore of the ferrule;
the deformed portion of the tube is sized and shaped to pass through a guidewire lumen of a catheter;
the elongated optical guidewire assembly includes an optoacoustic imaging probe portion, proximally terminated at the oblique angle beveled first end, and a system connector lead portion, proximally terminated at the oblique angle beveled second end; and
the optical fibers are secured within the deformable tube using a flowable and hardenable substance.

* * * * *

UNITED STATES PATENT AND TRADEMARK OFFICE
CERTIFICATE OF CORRECTION

| | | |
|---|---|---|
| PATENT NO. | : 8,583,218 B2 | Page 1 of 3 |
| APPLICATION NO. | : 12/609123 | |
| DATED | : November 12, 2013 | |
| INVENTOR(S) | : Michael J. Eberle | |

It is certified that error appears in the above-identified patent and that said Letters Patent is hereby corrected as shown below:

On the Title Page

Item (56) in column 2, under "Other Publications", line 7, delete "09745242.9-Exam" and insert --09745242.9, Exam--, therefor In the Drawings Sheet 4 of 14, Fig. 3B, reference numeral 300, delete "300" and insert --310--, therefor (See Attached Sheet)

In the Specification

In column 3, line 56, delete "there between" and insert --therebetween--, therefor In column 4, line 1, after "show", insert --an--, therefor In column 4, line 6, delete "FIG." and insert --FIGS.--, therefor In column 4, line 18, delete "guide wire" and insert --guidewire--, therefor In column 10, line 4, delete "401B" and insert --401A--, therefor In column 10, line 23, after "abutment", insert --.--, therefor In column 11, line 28, delete "401B 811A" and insert --401B, 811A--, therefor In column 13, line 3, delete "FIG." and insert --FIGS.--, therefor <div style="text-align:right">
Signed and Sealed this<br>
Twelfth Day of August, 2014
</div>

<div style="text-align:right">
Michelle K. Lee<br>
<em>Deputy Director of the United States Patent and Trademark Office</em>
</div>

In column 13, line 29, delete "guide wire" and insert --guidewire--, therefor

In column 13, line 52, delete "guide wire" and insert --guidewire--, therefor

In column 14, line 11, delete "in to" and insert --into--, therefor

In column 14, line 19, delete "guide wire" and insert --guidewire--, therefor